(12) United States Patent
Erickson

(10) Patent No.: US 10,582,670 B2
(45) Date of Patent: Mar. 10, 2020

(54) INTEGRATED GAS AND LIGHT SYSTEM WITH MULTI-MEDIA IRRIGATION TECHNOLOGY

(71) Applicant: Stewart E. Erickson, Hudson, WI (US)

(72) Inventor: Stewart E. Erickson, Hudson, WI (US)

(73) Assignee: The Agricultural Gas Company, Petaluma, CA (US)

( * ) Notice: Subject to any disclaimer, the term of this patent is extended or adjusted under 35 U.S.C. 154(b) by 83 days.

(21) Appl. No.: 15/731,221

(22) Filed: May 4, 2017

(65) Prior Publication Data

US 2018/0000024 A1 Jan. 4, 2018

Related U.S. Application Data

(60) Provisional application No. 62/331,592, filed on May 4, 2016.

(51) Int. Cl.
| | | |
|---|---|---|
| *A01G 25/02* | (2006.01) | |
| *A01G 7/02* | (2006.01) | |
| *A01G 17/06* | (2006.01) | |
| *A01G 7/04* | (2006.01) | |
| *B05B 1/20* | (2006.01) | |
| *A01G 25/06* | (2006.01) | |

(52) U.S. Cl.
CPC .............. *A01G 25/02* (2013.01); *A01G 7/02* (2013.01); *A01G 7/045* (2013.01); *A01G 17/06* (2013.01); *B05B 1/20* (2013.01); *A01G 25/06* (2013.01); *A61M 2205/7536* (2013.01)

(58) Field of Classification Search
CPC ...... A01G 25/02; A01G 25/023; A01G 25/06; A01G 7/02; A01G 7/045; A01G 9/249; A01G 9/26; B05B 1/20–207; F16L 11/22; F16L 55/07; A01C 23/042
USPC ............ 239/450, 542, 549, 566; 405/43, 45; 47/48.5
See application file for complete search history.

(56) References Cited

U.S. PATENT DOCUMENTS

| | | | | |
|---|---|---|---|---|
| 2,802,530 | A * | 8/1957 | Kaufman ............... | A01G 25/02 264/156 |
| 3,603,511 | A * | 9/1971 | La Pierre ............... | A01G 25/02 239/276 |

(Continued)

OTHER PUBLICATIONS

Goorahoo, Cassel, Carstenson, Ashkan, Crop Growth Enhancement with CO2 Injection into the Crop Canopy with Drip Irrigation, CIT Final Report—Apr. 2003.

(Continued)

*Primary Examiner* — Cody J Lieuwen
(74) *Attorney, Agent, or Firm* — Skinner and Associates; Joel Skinner

(57) ABSTRACT

A multi-media irrigation device is disclosed. The multi-media device is a multi-channel emitter device for plant growth. It includes a substrate; a water channel disposed on the substrate, the water channel having a plurality of perforations; a gas channel disposed on the substrate, the gas channel having a plurality of perforations; and at least one further fluid channel disposed on the substrate and having a plurality of perforations. Also disclosed is an integrated, self supporting elevated gas delivery tube and LED light for crop foliage. Lastly, a system for delivery of CO2 gas to light-deprivation operation of *cannabis 'production is disclosed.*

10 Claims, 15 Drawing Sheets

SUBSTRATE PERFORATIONS ALLOW LINES TO BE SEPARATED IN THE FIELD

(56) References Cited

U.S. PATENT DOCUMENTS

| | | | |
|---|---|---|---|
| 4,842,204 A * | 6/1989 | Debruhl, Jr. ........... | A01G 25/09 |
| | | | 104/91 |
| 5,409,508 A | 4/1995 | Erickson | |
| 5,682,709 A | 11/1997 | Erickson | |
| 6,108,967 A | 8/2000 | Erickson | |
| 6,237,284 B1 | 5/2001 | Erickson | |
| 6,874,707 B2 * | 4/2005 | Skinner .................. | A01G 17/02 |
| | | | 239/542 |
| 8,770,888 B2 * | 7/2014 | Helbig ................... | A01G 25/06 |
| | | | 239/63 |
| 9,480,207 B2 * | 11/2016 | Tanase ................... | A01G 7/045 |
| 2008/0101863 A1 * | 5/2008 | Gesser ................. | A01C 23/042 |
| | | | 405/37 |
| 2011/0179705 A1 * | 7/2011 | Sinda ..................... | A01G 25/02 |
| | | | 47/48.5 |
| 2016/0198640 A1 * | 7/2016 | Singh ..................... | A01G 7/045 |
| | | | 362/96 |

OTHER PUBLICATIONS

Hsiao, Molina, Matista, Qiu, Assessing CO2 Enrichment of Air Adjacednt to Crop Canopies in the Field, Final Report, Mar. 28, 2003.

Shrestha, Ashkan, Goorahoo, Carstensen, Crop-Weed Competition as Influenced by Elevated CO2, University of CA.

* cited by examiner

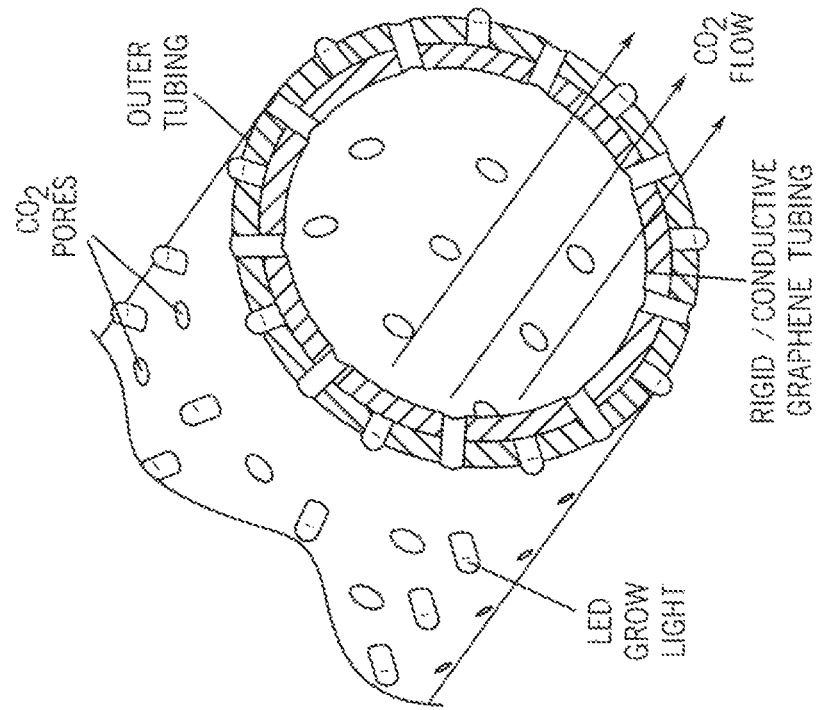
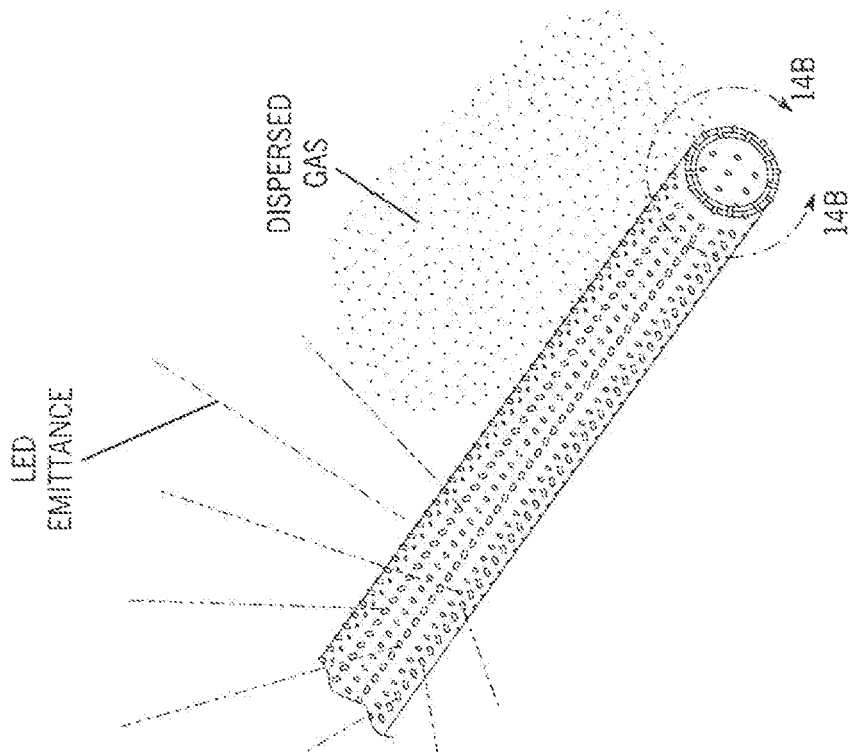
FIG. 14A
FIG. 14B

INTEGRATED GAS AND LIGHT SYSTEM WITH MULTI-MEDIA IRRIGATION TECHNOLOGY

CROSS-REFERENCE TO RELATED APPLICATIONS, IF ANY

This application claims the benefit under 35 U.S.C. § 119(e) of co-pending U.S. Provisional Patent Application Ser. No. 62/331,592, filed May 4, 2016, U.S. Provisional Patent Application Ser. No. 62/367,276, filed Jun. 27, 2016, and U.S. Provisional Patent Application Ser. No. 62/475,258, filed Mar. 23, 2017, which are hereby incorporated by reference.

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to agricultural systems, apparatus and methods. Particularly, the invention relates to:
an improved irrigation element, system, and method;
a system of delivering gases and light to crops. Most particularly, the invention relates to an integrated, self-supporting gas delivery and LED lighting system tor crops; and
an integrated, self-supporting gas delivery and LED lighting system for *Cannabis*

2. Background Information

Existing technology in this field is believed to have significant limitations and shortcomings. For this and other reasons, a need exists for the present invention.

All US patents and patent applications, and all other published documents mentioned anywhere in this application are incorporated by reference in their entirety.

BRIEF SUMMARY OF THE INVENTION

The invention provides an irrigation element, system and method which are practical, reliable, and efficient, and which are believed to fulfill the need and to constitute an improvement over the background technology.

In one aspect, the invention provides a multi-channel emitter device for plant growth, comprising
a substrate;
a water channel disposed on the substrate, the water channel having a plurality of perforations;
a gas channel disposed on the substrate, the gas channel having a plurality of perforations; and
at least one further fluid channel disposed on the substrate and having a plurality of perforations.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 14A is a perspective view of a portion of an integrated gas delivery and LED light emitting tube.

FIG. 14B is a crossectional view of the tube.

DETAILED DESCRIPTION

I. Multi-Media Irrigation

Figure 1:
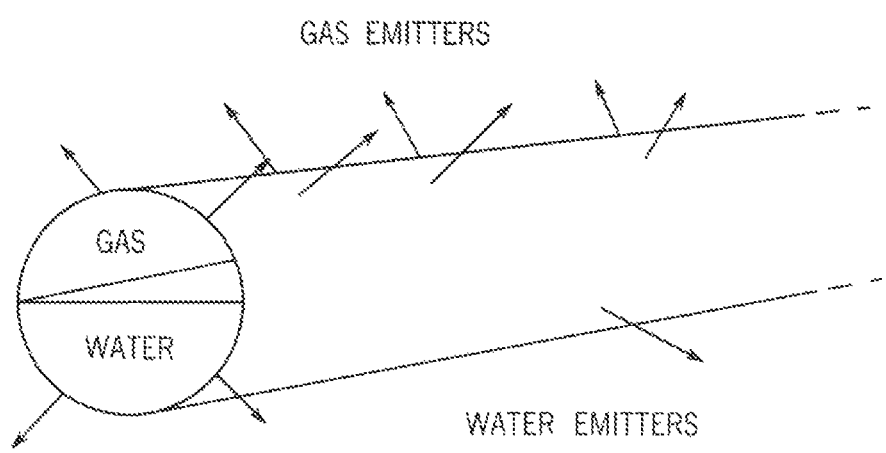
FIG. 1 illustrates one embodiment of the element of the invention.

1. Multiple Channel Tube for Irrigation Water and Gas Deliveries

The invention provides a Multiple Channel Tube for Irrigation Water and Gas Deliveries. At least two channel tape/tube is provided to facilitate optimum delivery of irrigation water and aerial gases to plants. The tube is manufactured in a single extrusion process and has shared walls generally made of PVC or some like material. The single tape or tube has two elongated annual spaces with openings at routine along its length. The openings for water emissions are position at a different interval (usually shorter) than the interval than the spacing of emitters connected to the annual space conducting the gas for aerial release.

The position of the emitters may generally be opposite 180 degrees along the sides of the annual spaced as the water is to be directed in to the ground for the plants roots and the aerial gas is desired to be directed skyward towards the plants foliage.

The emitter flow rates may be substantially different to accommodate optimum water delivery for a given crop and optimum gas delivery for a given crop.

The gas emitters may have a spigot/nipple that will accommodate ancillary extension hoses or apparatus like a trellis of the present inventor to further direct the gas directly to the foliage of the plant.

The present invention may also include a single channel tube with such nipples and spigots that will accommodate ancillary extension hoses or apparatus like a trellis of the present inventor to further direct the gas directly to the foliage of the plant when water deliveries are not desired or when there is already an irrigation tube permanently installed in and orchard or vineyard or the likes.

Current irrigation tubes/tapes designs may not result in optimum gas distribution or efficiency of delivery of more expensive gases.

The invention is useful for aerial optimization for crops focusing on $CO_2$ benefits. The problem is affordably operating gas delivery through irrigation systems designed to accommodate water. Many crop-planting pattern and spacing, notably orchards, the water requirement patterns are significantly depart from an optimal gas delivery pattern. The present inventor noted it would be best to deliver gas to plants foliage from the inside out—rather than from the outside in. Laying tape is irrigation tape is expensive so it became apparent that a single tape with tow conduits would be desirable.

Advantages of this aspect of the invention include, but are not limited to:
  Single manufacturing process. Lower manufacturing labor and materials.
  Less labor to deploy and retrieve tapes.
  Ability to do inside out foliar gas delivery using extension apparatus.
  More efficient gas delivery
  Don't have to re-sequence water deliveries to accommodate gas deliveries. It can water and pump gas at the same time.
  If pumped water and gas at same time would conserve thermal integrity of gas when using it for frost and freeze prevention.
  Can lay gas only lines that accommodate orchard hook ups with ancillary foliar hook ups.

2. Multiple Channel Tube for Irrigation Water and Gas Deliveries

The invention also provides Micro-Tubes tor Delivery of $CO_2$ and other Beneficial Gases to Crops. A micro-tube design is provided for widespread distribution of $CO_2$ and other beneficial gases to agricultural crops and trees (all such gases shall be referred, to herein as "$CO_2$"). The invention is comprised of a tube (1) into which $CO_2$ is injected, (2) which remains inflated down its entire length with gas pressure as low as 5 psig, (3) which dispenses $CO_2$ substantially uniformly down its entire length. The tube can be either (a) similar to currently available water irrigation tapes but with emitters or holes either more widely spaced, smaller in diameter, and/or otherwise more restrictive to the flow of $CO_2$, or (b) comprised of a material that allows $CO_2$ to seep out into the atmosphere.

Micro-irrigation tubes currently available in the marketplace offer efficient, widespread distribution of irrigation water. While these micro-irrigation tubes are well suited for irrigation and have been used by The Agricultural Gas Company and AG Gas$^{SM}$, L.P. for distribution of $CO_2$ (gas-only) deliveries, even the micro-irrigation tubes with the lowest flow specifications are effective distributors of gases only at relatively high pressures used to achieve relatively high target $CO_2$ concentrations in the field, and are not perfectly suitable when low target $CO_2$ concentrations are appropriate for the extant field conditions. The resulting problem is a volume and pressure discrepancy between the crops' irrigation water requirements and delivery thereof, versus achieving a desirable & effective elevation of $CO_2$. This is because the gaseous products, including $CO_2$, have very different compression characteristics, fiction loss, and other physical parameters than water, thus affecting the micro-tube's desired transmission characteristics.

Currently, some companies such as Queen Gil an Israeli company produce the lowest flow micro-irrigation product on the market. Flow rate for Queen Gil ultra-low-flow micro-tube is 0.053 GPH (individual emitter), with an 8-inch emitter spacing resulting in 0.13 gallons per minute per 100 feet. There are 150 emitters per 100 feet for 8" spacing. Typical low flow tapes, such as Toro's lowest flow micro-tube, distributes 0.1.3 GPH, with 8" emitter spacing, resulting in 0.34 gallons per minute per 100 feet.

Even at these lowest flow rates for irrigation water, these micro-tubes and their emitters allocate gas flow at too high of a rate, and the desired pressures are not achievable i.e. too low of pressure to maintain a plus 100 ppm to plus 700 ppm $CO_2$ concentration with greater than 90% distribution uniformity.

Advantages of this aspect of the invention include:
1. Has a lower flow rate for gas than any product on the micro-irrigation market (less than the flow rate achieved through an irrigation tape with 0.053 GPU per individual emitter, with an 8 inch emitter spacing resulting in 0.13 gallons per minute per 100 feet.)
2. Has a smaller diameter micro-tube with emitters if necessary (less than ⅝ inch diameter)
3. Emitters' flow rate accommodates a higher recommend operating pressure in the tape of between 5-20 PSI, while achieving an average plus 50 ppm to plus 700 ppm $CO_2$-concentration in the open-field, with a greater than 90% distribution uniformity, up to a 1,200 foot length run, in winds less than 8 miles per hour
4. At desired operating PPM levels no greater than 3,500 scfh per hour (average) per acre
5. With less than 8 inch emitter spacing.
6. Achieving a plus 100 ppm to plus 700 ppm $CO_2$ concentration with greater than 90% distribution uniformity
7. Two tapes per standard 40 inch bed of strawberries (four rows of plants, or one tape per narrow bed of strawberries with 2 rows of plants, and 20 to 30 inch bed spacing for other field crops Upstream of the micro-tubes there are meters, valve, etc. that require pressure to operate effectively. The present invention allows other equipment that is available to work properly with $CO_2$ and other beneficial gas deliveries to fields. Further, the micro-tubes themselves need to be under pressure to properly "inflate" allowing transmission of gas down their entire length precluding kinks or bends that will disrupt the uniformity of gas distribution. Therefore, the present invention offers better pressure and resulting uniformity of gas distribution. This is especially essential for sub-surface application of the micro-tube where pressure from the soil will also tend to collapse the micro-tube disrupting gas transmission down the entire length: i.e. greater pressure is necessary within the micro-tube. Further, by having higher pressures in the system manifold pipe diameter can be reduced resulting in much cheaper costs to build and install gas delivery systems.

3. Improved irrigation Element

The invention also provides an irrigation element or structure for the delivery of fluids to a plant. The improved irrigation element or structure is for water and/or the delivery of one or more forms of gaseous media to a plant on one hand, and/or an improved irrigation element or structure for the select delivery of at least two fluids to a plant, advantageously, but not necessarily, a select delivery of both a liquid and a gas to a plant, on the other hand.

Aspects of this aspect of the invention include:

1. An improved irrigation element pressurizable uniformly throughout its length for dispensing a fluid via a plurality of orifices there through at a pressure minimum of about 1 psig as contemplated and/or shown herein and/or described above, including equivalents thereof.

2. An improved irrigation element characterized by multiple lumens for the select delivery of at least two fluids as contemplated and/or shown herein and/or described above, including equivalents thereof.

3. Where the lumens can be operated at individually different pressures, volumes and rates of delivery of fluids.

4. The multiple channels can be affixed using a substrate material.

5. In the preferred embodiment the adjoining substrate or walls of adjacent lumens is perforated (or sectional) so that the individual tubes can be easily separated from each other, allowing individual fluid quick hook-up to different supply manifolds and/or easy repairs or the likes.

6. The perforated substrate allows use of conventional irrigation stakes for easy staking to the ground.

7. The irrigation element maybe eliminated fa separate conventional line) if invention is used in aerial orchard application where it is desirable to keep the irrigation at the ground level far below the gaseous applications in the trees' canopy.

Figure 2:
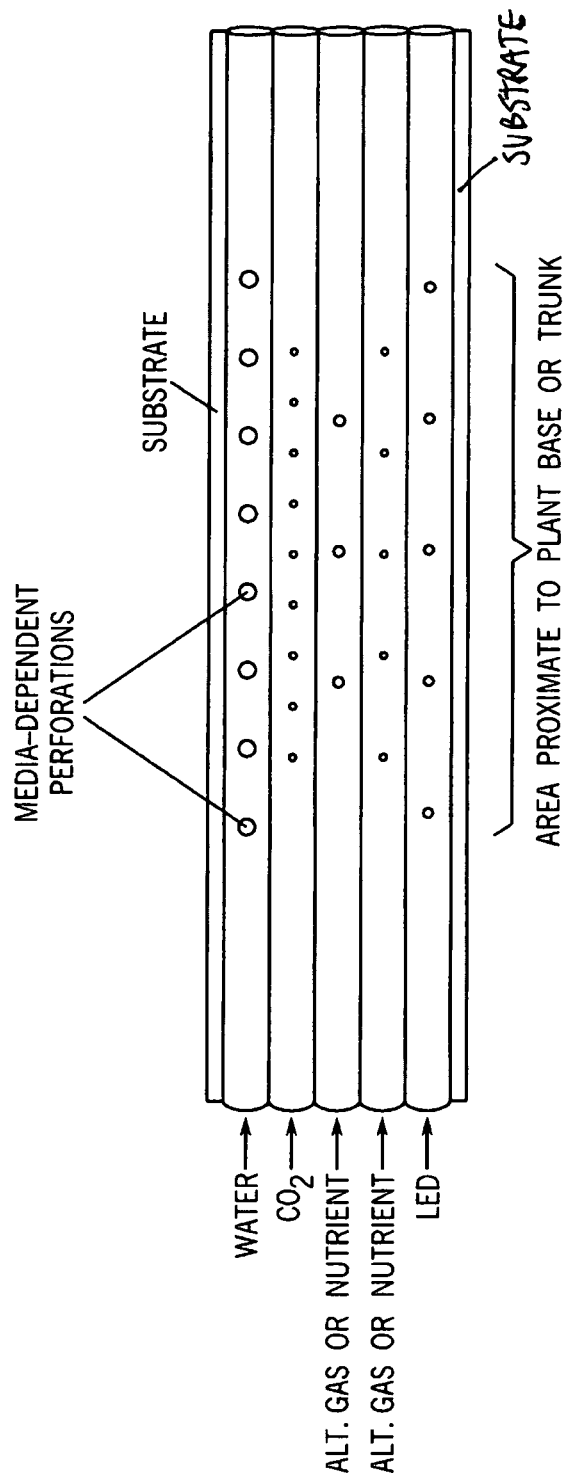
FIG. 2 shows an embodiment of a multi channel emitter tape for water, CO2 and three other media.
Figure 3:
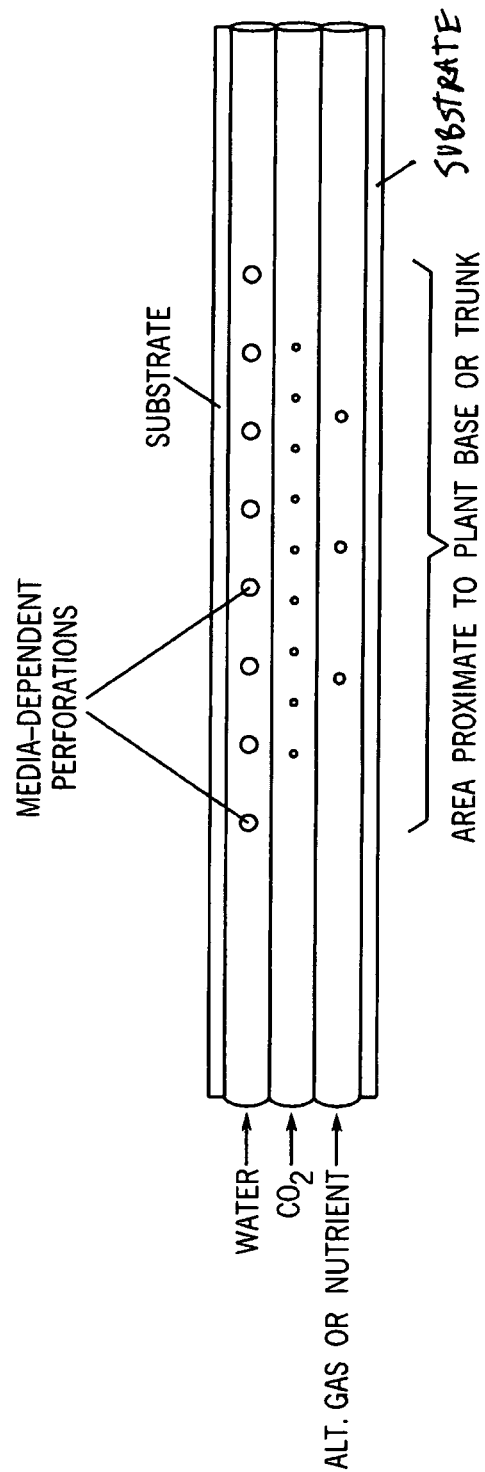
FIG. 3 shows an embodiment of a multi channel emitter tape for water, CO2 and one other media.
Figure 4:
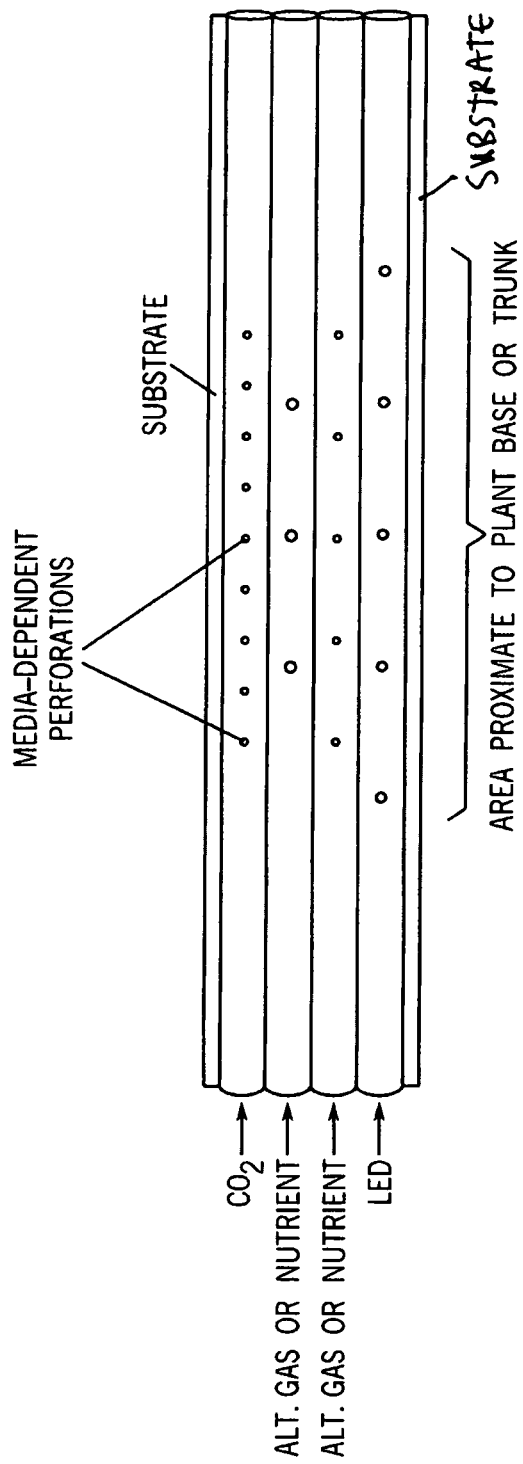
FIG. 4 shows an embodiment of a multi channel emitter tape for CO2 and three other media.
Figure 5:
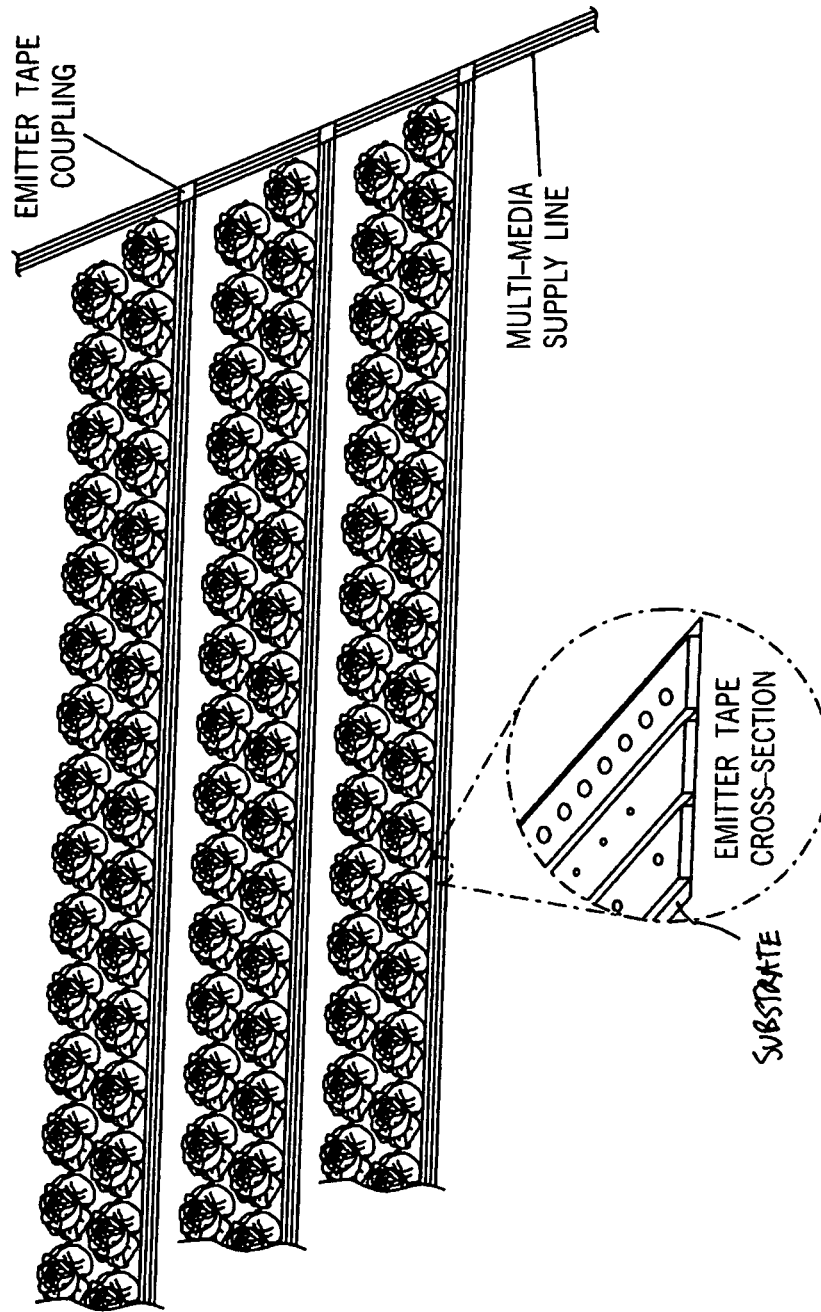
FIG. 5 shows an embodiment of a system including multi channel emitter tape with seasonal vegetable crops.
Figure 6:
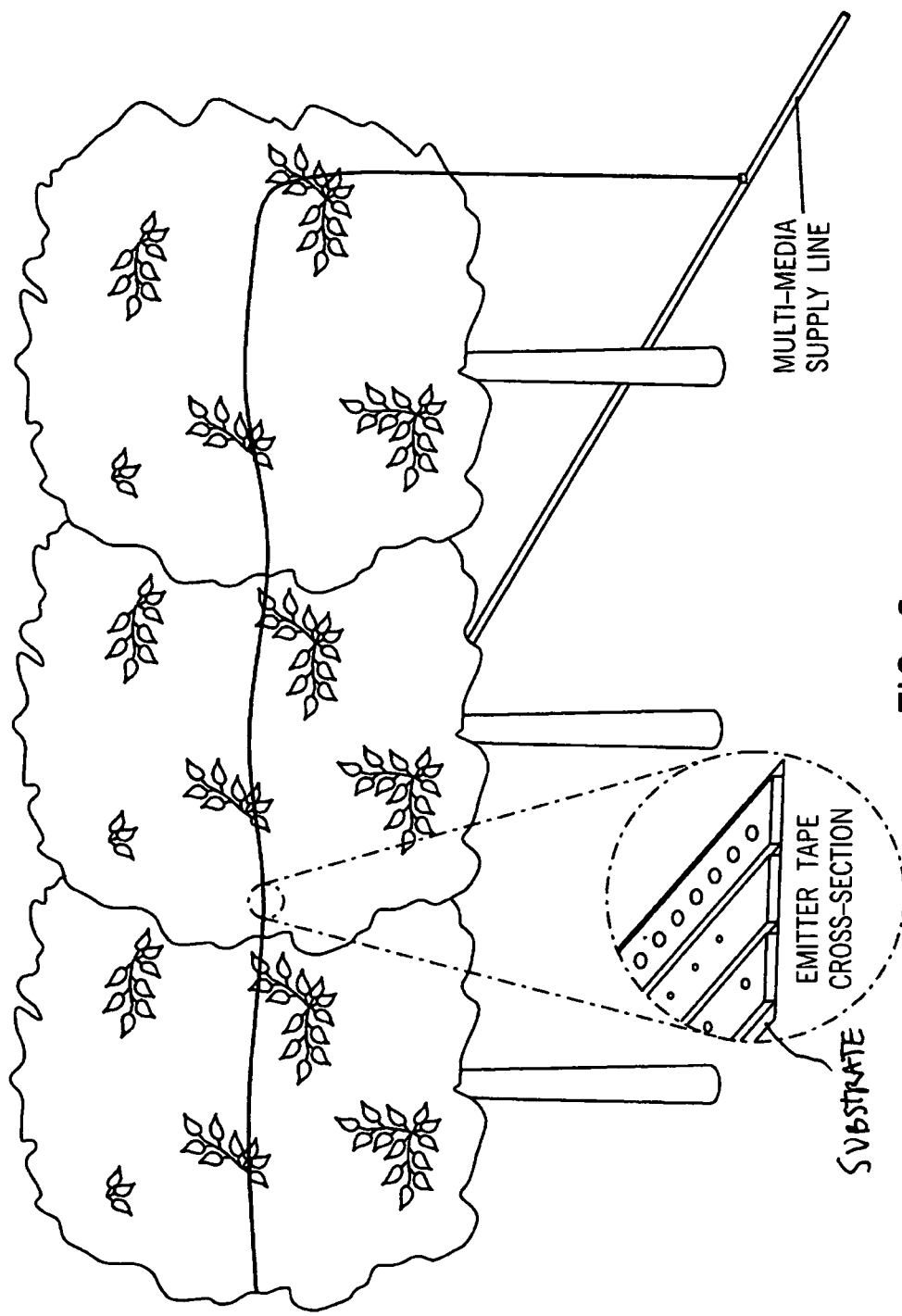
FIG. 6 shows an embodiment of a system including multi channel emitter tape used with a citrus hedgerow, in a side view.
Figure 7:
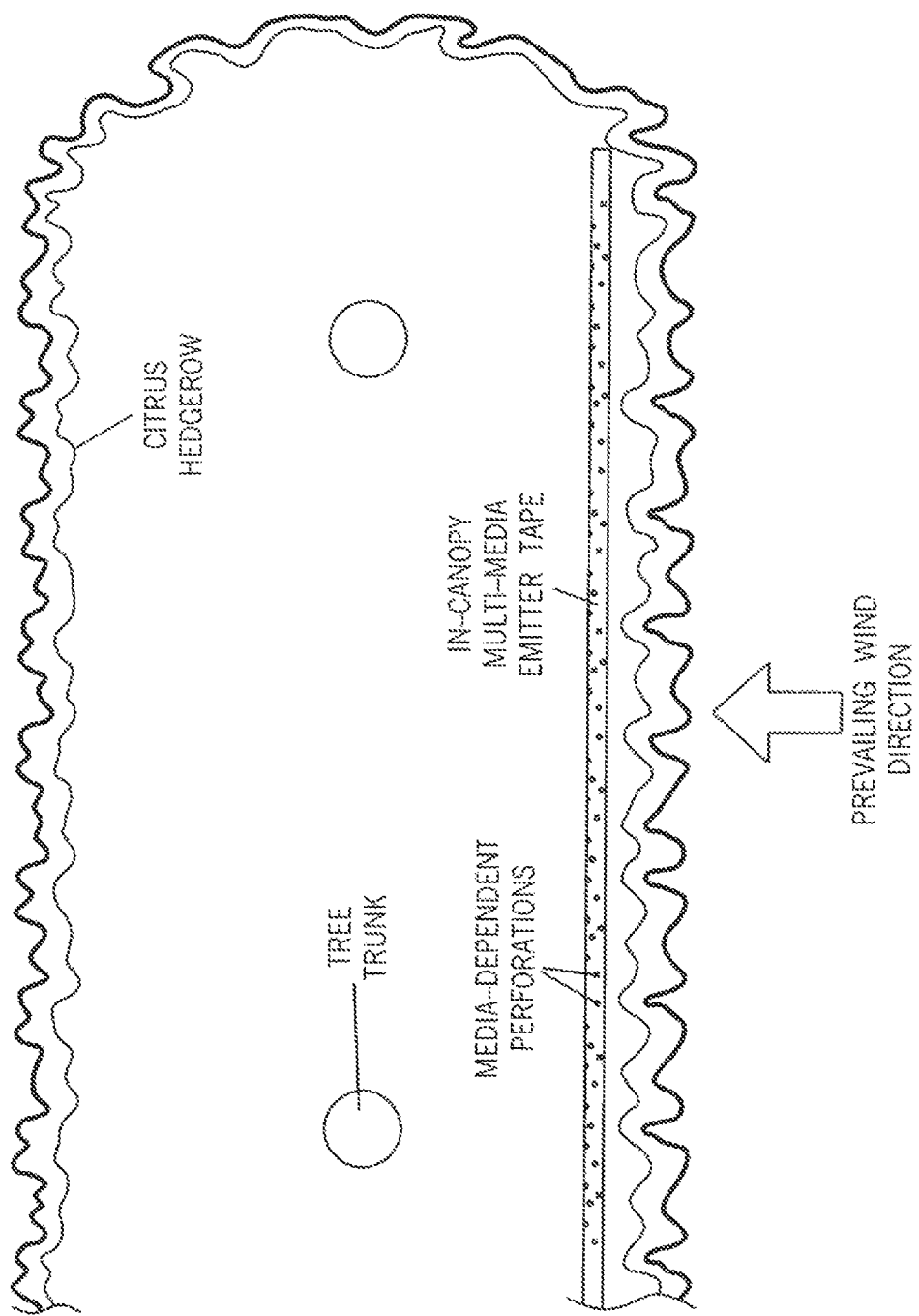
FIG. 7 shows the system in a top or plan view.
Figure 8:
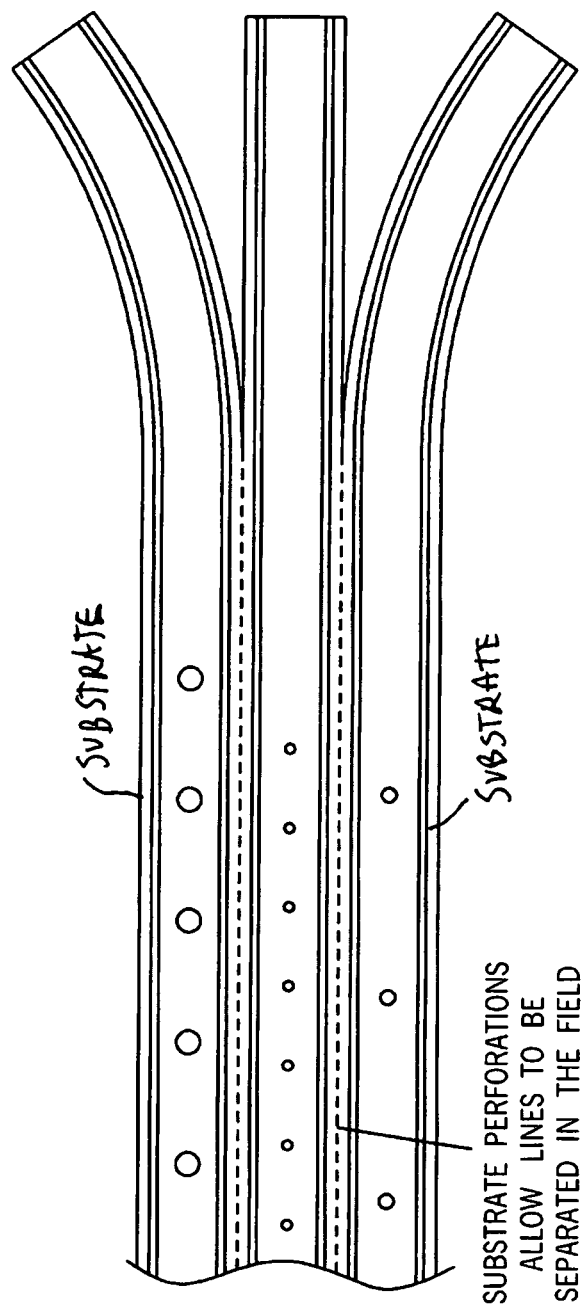
FIG. 8 shows an embodiment of a multi channel emitter tape with a detachable perforation, in a top view thereof.
Figure 9:
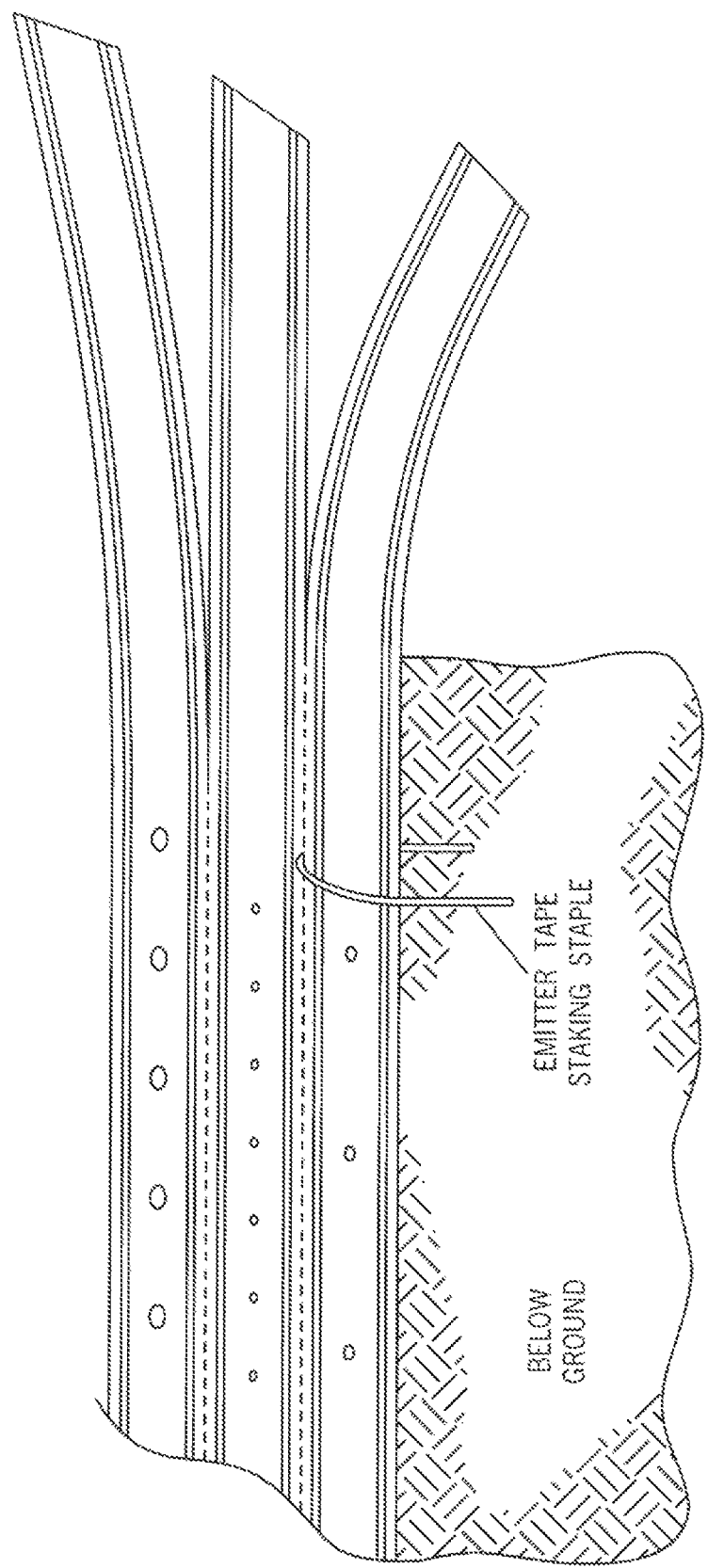
FIG. 9 shows the tape used with a staking staple.
Figure 10:
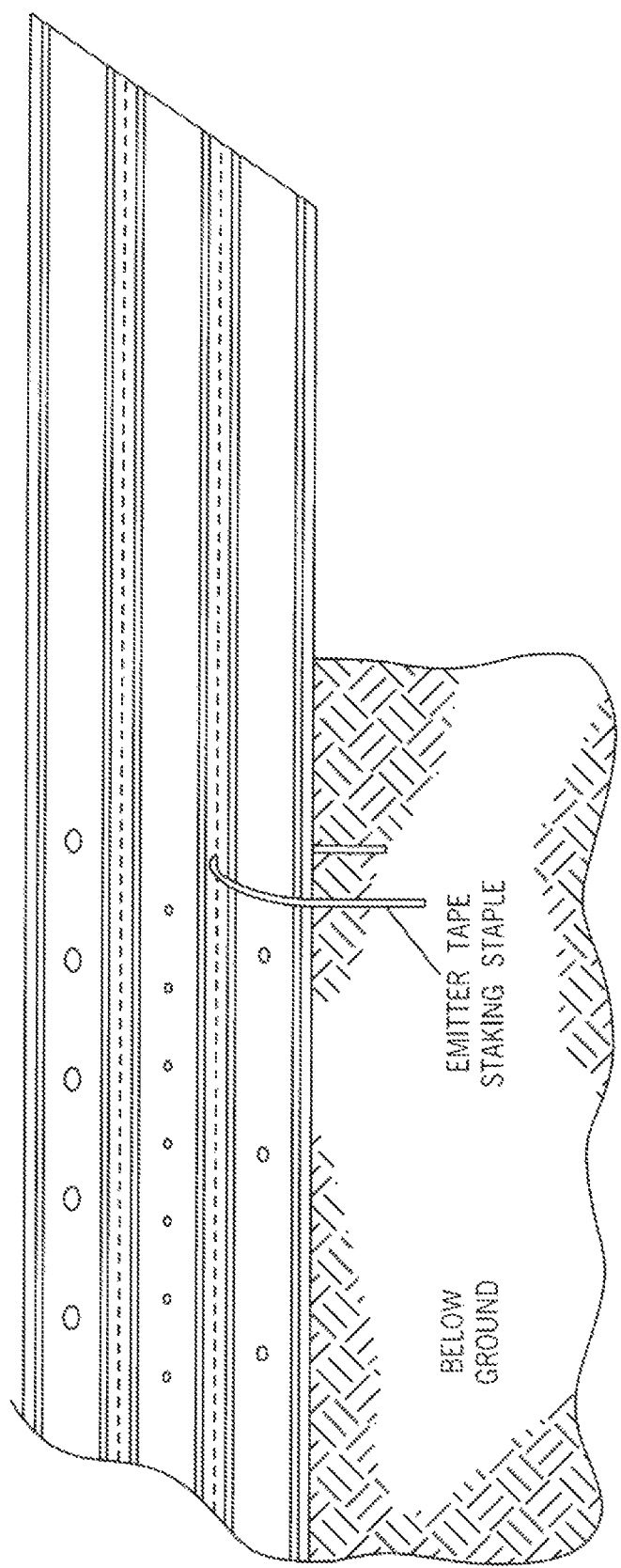
FIG. 10 is a further view thereof.

FIGS. 2-10 show several embodiments of irrigation elements having a tape like configuration. FIG. 2 shows an embodiment of a multi channel emitter tape for water, CO2 and three other media. FIG. 3 shows an embodiment of a multi channel emitter tape for water, CO2 and one other media. FIG. 4 shows an embodiment of a mufti channel emitter tape for CO2 and three other media. FIG. 5 shows an embodiment of a system including multi channel emitter tape with seasonal vegetable crops. FIG. 6 shows an embodiment of a system including multi channel emitter tape used with a citrus hedgerow, in a side view. FIG. 7 shows the system in a top or plan view. FIG. 8 shows an embodiment of a multi channel emitter tape with a detachable perforation, in a top view thereof. In this embodiment, the adjoining substrate or walls of adjacent lumens is perforated (or sectional) so that the individual tubes can be easily separated from each other, allowing individual fluid quick hook-up to different supply manifolds and/or easy repairs or the like. FIG. 9 shows the tape used with a staking staple. FIG. 10 is a further view thereof.

Factors of interest in design include, but are not limited to:
Shared annular wall or substrate
Perforated edge connecting the channels so they can be easily pulled apart or segregated for repair and affixing to different supply manifolds!!
A gas emitter desirably positioned at each plant
Water emitter faces down and gas emitter faces up
Single spool installation function
Single "stapling" function to connect tube to the ground
Gas emitter location is visibly labeled
Gas pipe is smaller diameter, lower flows rates and builds more back pressure II. Integrated, Self Supporting Elevated Gas Delivery Tube and LED Light for Crop Foliage The present invention provides a device and method for delivering enriched gaseous medium, such as $CO_2$ enriched gas, oxygen deprived gas, thermally treated air, or pheromones, to seasonal vegetable crops grown in beds (such as peppers and fresh market tomatoes) and to permanent crops grown in hedgerows like tea, coffee, viticultural practices (raisins, wine or table) or orchards, notably trees grown in hedgerows like mandarin oranges that may require or desire a vertical trellis or staking. The gas is delivered to the vertically supported vines through a stake or trellis that incorporates an annular space dedicated tube for gas vertical deliveries to foliage supported by the device.

Figure 11:
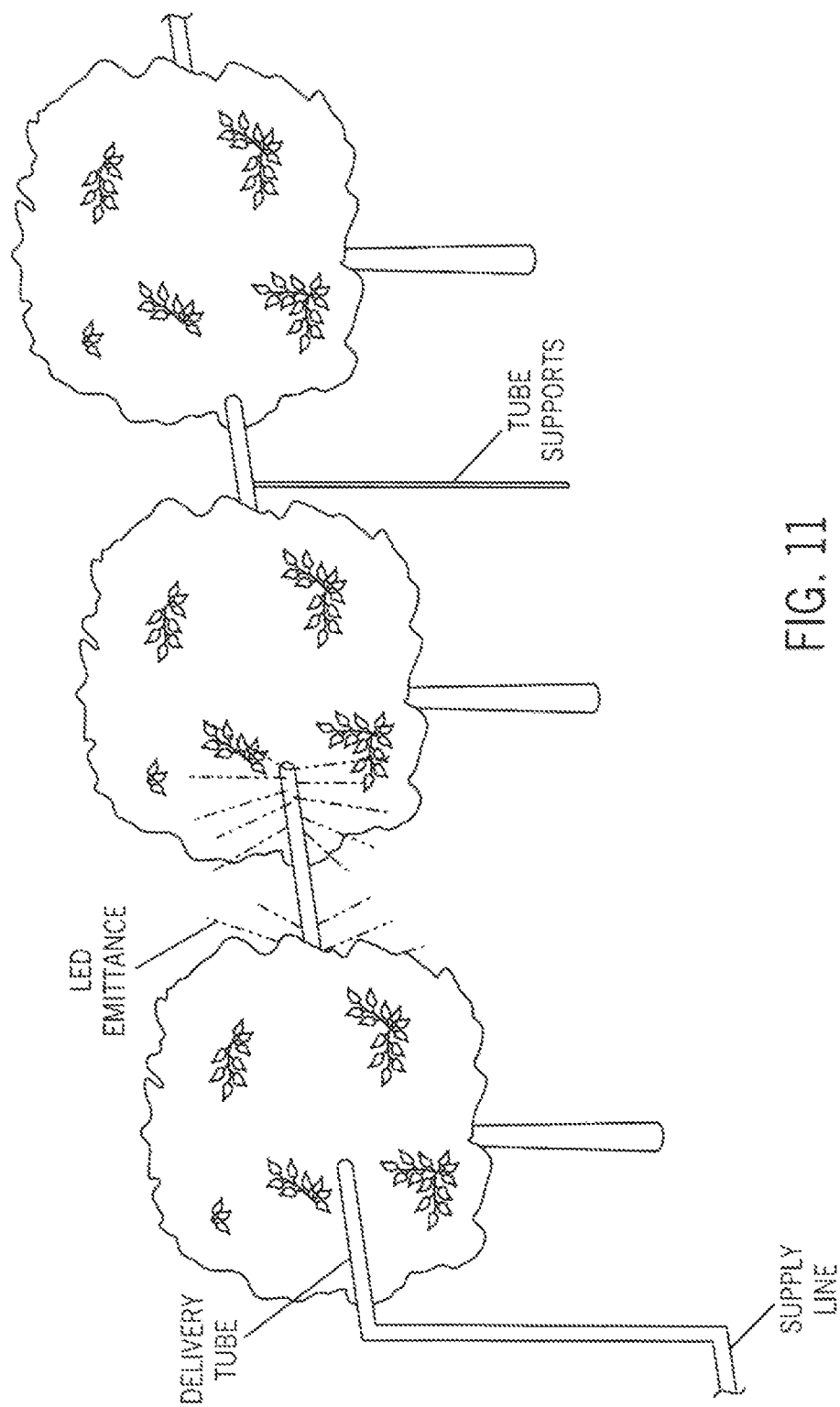
FIG. 11 illustrates an embodiment of the integrated, self supporting gas delivery and light emitting system of the invention, operatively deployed In an orange orchard

FIG. 11 illustrates an embodiment of the integrated, self supporting gas delivery and light emitting system of the invention, operatively deployed in an orange orchard. FIG. 2 illustrates an embodiment of the system deployed in a grape vineyard.

Figure 12:
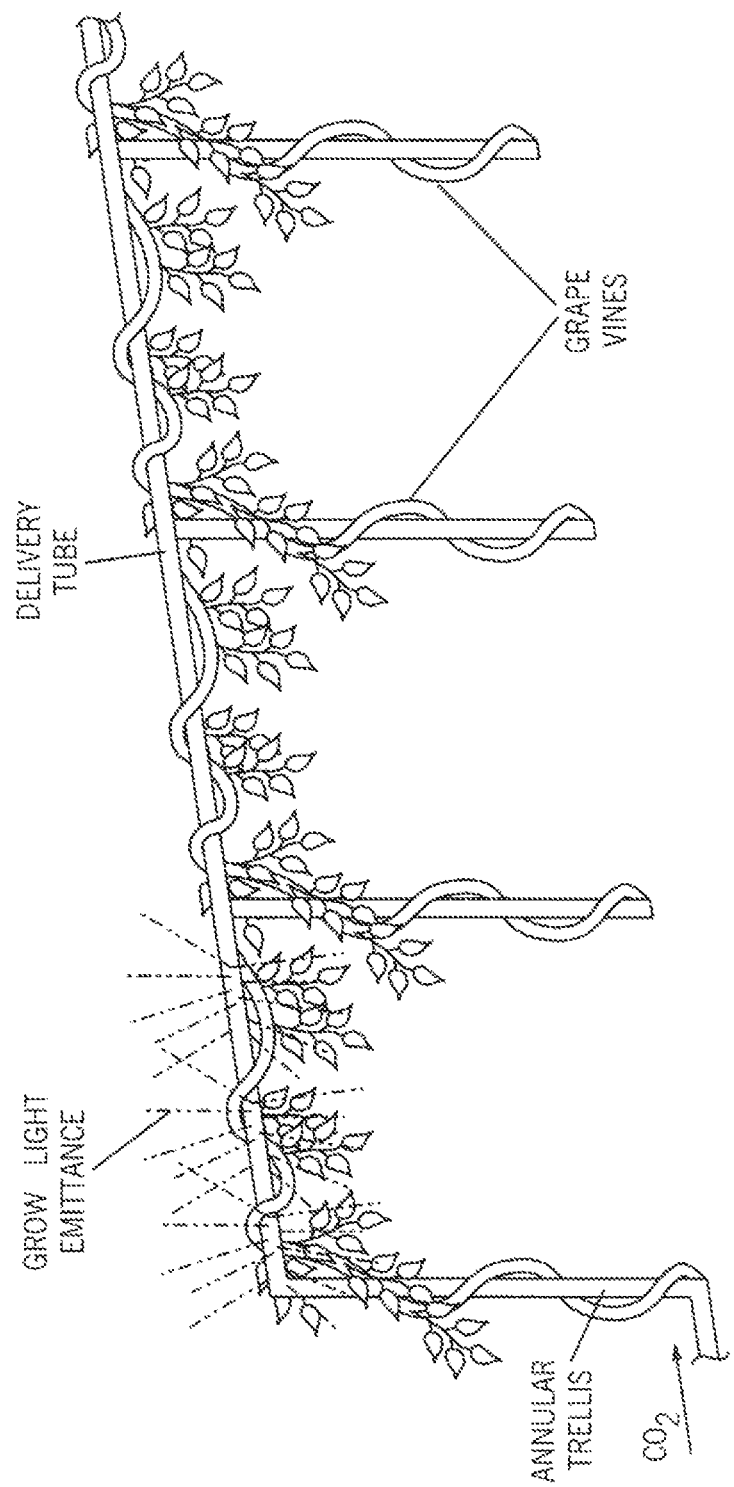
FIG. 12 illustrates an embodiment of the system combined with a plurality of CO2 emitters.
Figure 13:
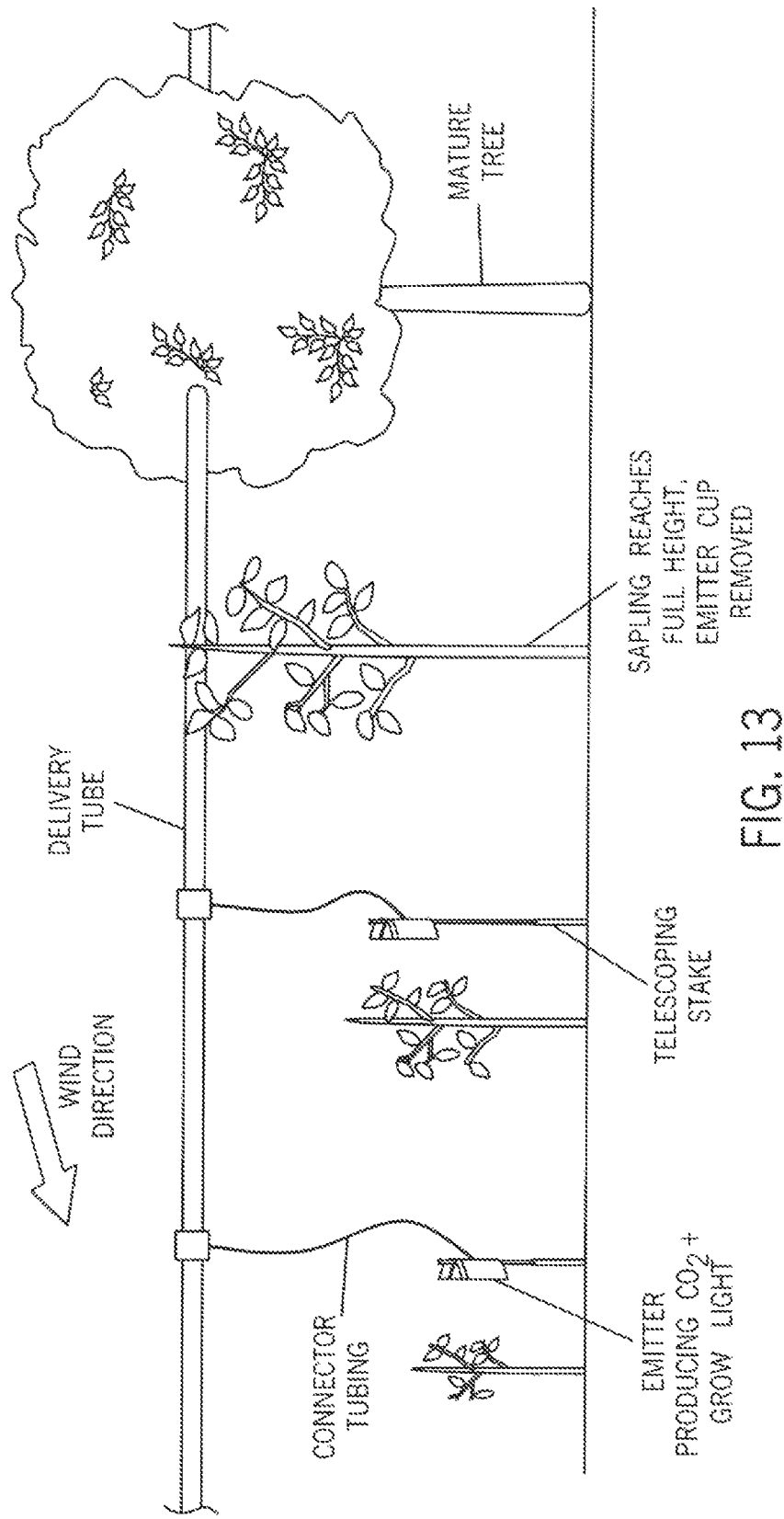
Figure 15:
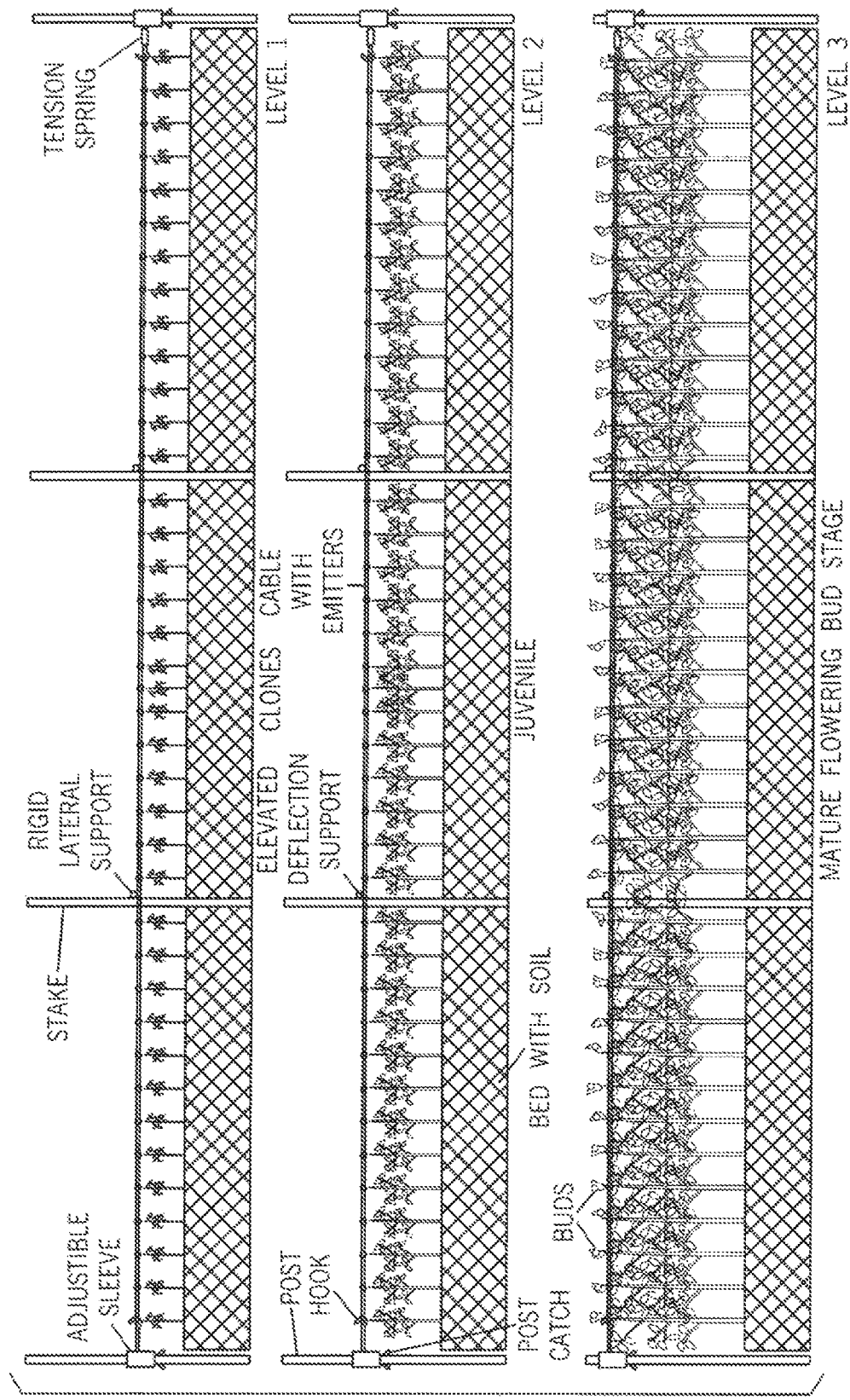
FIG. 15 illustrates one embodiment of the system of the invention.

FIG. 12 illustrates an embodiment of the system combined with a plurality of CO2 emitters. An ex ample of the CO2 emitter is disclosed in Applicant's pending U.S. patent application Ser. No. 15/153,038, filed May 12, 2016 entitled Arial Fluid Application Technology for Orchards, Vineyards and the Like.

FIG. 14A is a perspective view of a portion of an integrated gas delivery and LED light emitting tube. FIG. 14B is a crossectional view of the tube.

In the orchard industry, typically micro sprayers are used to cover and area of soil to promote widespread root growth of the trees, which is favorable for the good health of the trees. In the invention both the light and enriched gas (CO2, thermally treated air, pheromones or the like) are delivered more closely to the canopy/foliage of the vertical foliage supported by a trellis or stake, comparatively to irrigation tubes that deliver water to the ground. When orchards are planted with saplings/juvenal tress there the foliage of the trees occupies a very small percentage of the overall acreage of the orchard or vineyard, because the saplings and/or juvenile crop have to be planted at great intervals to allow proper spacing whence the trees/crops grow to maturity and have extensive foliage canopies. Therefore, the invention includes a support trellis and/or stake that has an annular space to conduct gas for emission immediately adjacent to the foliage of the crop and integrated LED lights. The gas and light are emitted directly at the foliage rather that at ground level and allowed to disperse through the field. Further, since the foliage is elevated and continues to move upward with growth, from year to year for permanent crops, it is desirable to install the integrated gas and light supply tube in a vertically position to a future desired height in the crops future foliar canopy, and then provided a drop down flexible "spaghetti pipe" or the like with one or more emitters downward to the juvenile plant which is closers to the ground therein desirably releasing the gas directly to the area of the saplings' foliage, for example a young grape vine start. In the preferred embodiment, a gas and light supply line would be installed at an elevated position above the early stage foliar canopy and would have many emitters and diodes located along the entire length of the installation, but these emitters and diodes would be shut off/plugged with a removable plug during the juvenile years when the foliar canopy is below this supply line. A drop down tube would be installed directly above each juvenile plant, and be downwardly depending providing the proper length to reach from the elevated supply line down to the foliar leafy area of the juvenile plant. This drop down with one or more emitters and light emitting LED diodes is desirably adjusted on an annual or semiannual bases, to emit $CO_2$, other beneficial gases and light at corrected heights and length and emission rate to "match" the crop it attains vertical leafy growth and leafy canopy dimension. This can be accomplished by either retracting the tube upward, "J-Hooking" the tube, shortening it by cutting it to length, or restricting gas flow from the lower portion from the bottom up through rolling the tube up, capping, pinching or the like, below the leafy area. Additional emitters can be opened up to if the dimension of the canopy expands so that the gas will mirror and adjacently flow to the elevated leafy canopy. Eventually the drop down tube may be maybe desirably removed all together, when the foliar canopy reaches to main horizontally suspended supply line, like for grapes which then grow horizontally with little if any sub-canopy structure, or in the care of hedgerows crops it can be desirable to continue to release some gas and light into the lower canopy. These are commonly used in the orchard industry, vineyards, growing tomatoes or other crops that need vertical support. In the preferred embodiment, the emitter orifices from the annular space could be vertically arranged in either an open or closed position to accommodate different growth heights of the crops foliage. That is when the seedling is started and staked up the lower orifices would be opened and upper orifices would be closed thereby conserving gaseous emissions and pumping costs. As the crop matures and grows vertically upper orifices are opened adjacent to the foliage and lower orifices might be left open or closed, whichever, is most efficient for foliage exposure to gas enrichment.

Then, as in the case of vine crops that are trained to grow horizontally along a wire like vineyards, horizontal orifices are opened down the length to match the leafy area when the vines drape themselves horizontally as is preferred in mature grape production. This puts gas and light emissions in immediate proximity to crops' foliage where it is needed and desired to stimulate crop production.

Further, in the preferred embodiment one or more integrated supply lines are attached to the top wires of a wine trellis or orchard trellis.

An aspect of the invention is that the horizontal length of the supply line plastic tube usually polyethylene tubing has graphene impregnated into the extruded plastic down its length in entirety giving the tube sufficient tensile strength so as to be self-supporting, so that a steel wire is not need to support the tube and/or to create a trellis tor the vine or crop to attach to. The graphene or electrical conducting material also acts as the electricity transmission conduit to illuminate the LED diodes down the entire length of the tube deployed in a field of crops.

The device and method may be used in conjunction with an Aerial Application manufactured and sold by AGGas of Hudson, Wis., USA, as the supply to the wind foils only in this ease the supply would come from above. This would be desirable also because it would hold the drop down tube in a steady position not be blown by the wind. And, the wind foils act as a housing unit contain illuminating LED diodes that face the sapling tree or the likes, to further enhance the growth.

The drop down tube should be rigid or tethered so as not to be blown out of its upwind emitter position in relationship to the leafy canopy The invention has many benefits. Trucks deliveries of $CO_2$ are typically three times as expensive as gas via pipeline, so would cost substantially less. The method should conserve significant amounts of costly $CO_2$ get more $CO_2$ to the seedlings and crop foliage for use, utilize and existing orchard, vineyard and crop accepted devices, conserve a lot of pumping energy for pumping gas that would otherwise disperse into the atmosphere. The method should conserve a lot of costly gas. And, the method is agronomically correct for existing farming functions without disruption to the farmers. This allows gas to get to the elevated leafy canopy that is fully exposed to sunlight which is where most of the photosynthesis occurs.

Viticultural practices require some 30 or more miles of wire per 640 acre section. The present invention eliminates or reduces the need for wire, while gaining increased crop production. It is well known in the sciences the plants can increase crop growth with additional light in certain bandwidths/colors and through increased duration of light. This is common practice in greenhouse. However, to date it has been inefficient and uneconomical to add light in the outdoor environs where most crops are grown. Further it is well know that crops in the major production areas "shut down" for large portions of the daylight growing hours due to extreme high temperatures like California. Therefore, it is desirable to take advantage of the plantings and conducive temperature during morning and evening hours to stimulate crop production by introducing light into the equation.

The present invention provides and integrated system for both gas, light and water additives to provide economic cost efficiencies so that growers can take advantage of this opportunity to reduce water, make land more productive and grow healthier crops.

Pivot irrigation uses drop down tubes for the delivery of water. While not completely dissimilar in appearance, that product is completely deficient for watering of grapes, orchards etc., and the gas has to be continuously delivered over the entire acres in a grid work of permanently installed supply lines not a single row mobile wheeled irrigation systems. Would allow direct application of $CO_2$ to the foliage of saplings and juvenile vines as they grow vertically. Growth of these immature trees is very essential and the economics would be greatly enhanced if the new orchard, vineyards and crops could be brought Into greater production at an earlier date. Further, because the young orchards, vineyards and crops have to provide wide spacing between the seedlings and the soil/ground is very susceptible to wind and heat from direct sunlight, which furthers water losses, which is costly, and can stress the immature plants. New seedlings are also more susceptible to mortality; draught disease, etc. so by "pampering" the saplings with $CO_2$ the overall economics off the orchard industry can be greatly increased.

Once mature crops have specific spacing and some are open grown wither for mechanical needs or for the needs of the crop itself. A good example is wine grapes, which have large spacing between rows of vines.

At maturity the vertical gas needs would be provided without any nuisance and interference of upwardly depending supply lines into trees, like nut trees, that have mechanical shakers that need to engage the trucks of the trees and would cut the upwardly depending supply lines.

Although the invention has been described and shown with elevated gas delivery and LED lighting integrated, it is within the purview of the invention that elevated gas delivery may be implemented independent of LED lighting, and that LED lighting may be implemented independent of elevated gas delivery.

III. System Delivery of $CO_2$ Gas to Light-Deprivation Operation of *Cannabis* Production Referring to FIG. 15, one embodiment of the system of the invention comprises one or more posts which are securely anchored to the ground at each end of the beds. The posts are constructed and arranged such that they will not bend, even when inward pressure is applied to the top of the post. A wire is extended the length of the row and attached to the corresponding post at the far end of the bed. Preferably, the wire element is a self supporting gas pipe disclosed in the patent documents Incorporated by reference herein. The wire is connected on each end to an adjustable sliding sleeve that can slide up or down on the post. The sleeve has the ability to lock or maintain to a fixed elevated position, that is height on the post, and is easily repositioned upwards or downwards to a new position as needed. The wire is tensioned generally tautly using any number of commercially available tensions like a ratchet strap, inducing minimal deflection down the length of the row from the far end post which also has the same slider arrangement. Cross members or aerial ties can be used intermittently down the row to support deflection in the wire emitter run as desired, for example a 3-20 foot spacing to create a scallop effect down the length of the row, but generally supporting the emitters at an equally desirable height at or just above the top of the plants from one end of the bed to the other.

Emitters and gas supply are supplied-down the length of the wire/bed row. Emitters are positioned just above the canopy of the crop. As the crop grows, the sliders at each end are moved up the posts as need to accommodate plant growth and to stay clear of the introduction of mesh trellis in the bed as is commonly known and used in the cultivation of *cannabis* or other such crops.

Rigid to semi-rigid emitters are suspended just at or above the leafy canopy of a single plant or row of the crop. Upward mobility of the device is permitted to correspond to plant growth. They may be removed or moved out of the way to facilitate harvest and other agronomic functions like the introduction of mesh.

The system of the invention can be extended to the control of pests such as mites. The infested plants can be tented with a sealed plastic fabric cover and the gas is introduced for a period of around 15 minutes at higher concentrations above 10,000 PPM to organically kill all of the pests on the plants. Multiple plants in that garden can be tented at once and a whole group can be cleansed of pest at once either through a single tent or multiple tents.

The system may incorporate applicants' multi-media irrigation technology to accommodate conductance of a variety of liquids, gases, aerosols, volumes and flow rates. Gaseous conductance can include thermally treated air, such as cooled air drawn across an ambient vaporizer present, and reverse flow direction for odor control and humidity control practices. Curtains can be provided between the rows of the system, to isolate vectoring and maintain a variety of gaseous mixtures between adjacent rows. Further, a pass through enclosure with gaseous enrichment from the system can even be provided to suppress vector transmission as people, equipment and supplies enter and leave the production area.

Applicants hereby incorporate by reference the disclosures of the following U.S. patent application:
Title: GROUND TO CANOPY GASEOUS MEDIA DELIVERY SYSTEM FOR CROPS INCLUDING LEAK DETECTION AND HOOK AND WAND FEATURES Application No.: 62/403,800 Filing Date: Oct. 4, 2016

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An elongated, multi-channel emitter device for distribution of Water, CO2 gas and light to enhance plant growth, and adapted to be placed in a plant canopy, comprising
a single, elongated substrate, the substrate having a first face;
a water channel disposed longitudinally on the first face of the substrate, the water channel having a plurality of perforations oriented away from the substrate for emitting water directly to an outside environment;
a CO2 gas channel disposed longitudinally on the first face of the substrate, the gas channel having a plurality of perforations oriented away from the substrate and adapted to omit CO2 gas directly to the outside environment;
a light channel disposed longitudinally on the first face of the substrate and having a plurality of Light Emitting Diodes (LEDs) which are disposed away from the substrate so that they are exposed to the outside environment, and
wherein the substrate has at least one longitudinally oriented set of perforations oriented relative to the water channel, CO2 gas channel, or the light channel, whereby such channel, respectively, may be separated from the other channels.

2. The device of claim 1, wherein the device has a tape like configuration.

3. The device of claim 1, wherein The water channel, gas channel and light channel are oriented parallel in each other.

4. The device of claim 1, wherein the water channel, gas channel and light channel each have a separate, independent input end for input of water, CO2 gas, and current, respectively, the input ends being disposed proximate to each other.

5. The device claim 1, further comprising at least one secondary fluid channel, the at least one secondary fluid channel transporting a gas of liquid fluid, the at least one secondary fluid channel being disposed on the first face of the substrate and having a plurality of perforations oriented away from the substrate for emitting a fluid directly to the outside environment.

6. The device of claim 1, wherein the water channel and CO2 gas channel comprises a lumen.

7. The device of claim 1, wherein the perforations of the water channel, the CO2 gas channel have a predetermined aperture size, the size of the CO2 gas perforations being lesser than the size of the water channel perforations.

8. The device of claim 1, wherein the substrate has two longitudinally oriented sets of perforations, one set of perforations being disposed between the water channel and the CO2 gas channel, and the other set of perforations being disposed between the CO2 gas channel and the light channel, whereby the channels may be selectively separated from each other.

9. An elongated, tape-like, multi-channel emitter device for distribution of water, CO2 gas and light to enhance plant growth, and adapted to be placed in a plant leaf canopy, comprising
- a single, elongated base substrate, the substrate having a first face;
- a water channel disposed longitudinally on the first face of the substrate, the water channel having a lumen and a plurality of perforations oriented away from the substrate for emitting water directly to an outside environment;
- a CO2 gas channel disposed longitudinally on the first face of the substrate, the gas channel having a lumen and a plurality o perforations oriented away from the substrate emitting CO2gas directly to the outside environment;
- a light channel disposed longitudinally on the first face of the substrate and having a plurality of Light Emitting Diodes (LEDs) which are disposed away from the substrate so that they are exposed to the outside environment;
- wherein the water channel, CO2 gas channel, and light channel are oriented parallel to each other; and
- wherein the substrate has at least one longitudinally oriented set of perforations oriented relative to the water channel, CO2 gas channel, or the light channel, whereby such channel, respectively, may be separated from the other channels.

10. An elongated, tape-like, multi-channel emitter device for distribution of water, CO2 gas and light to enhance plant growth, and adapted to be placed in a plant leaf canopy, comprising
- a single, elongated base substrate, the substrate having a first face;
- a water channel disposed longitudinally on the first face of the substrate, the water channel having a lumen and a plurality of perforations oriented away from the substrate for emitting water directly to an outside environment;
- a CO2 gas channel disposed longitudinally on the first face of the substrate, the gas channel having a lumen and a plurality of perforations oriented away from the substrate for emitting CO2gas directly to the outside environment;
- a light channel disposed longitudinally on the first face of the substrate and haying a plurality of Light Emitting Diodes (LEDs) which are disposed away from the substrate so that they are exposed to the outside environment;
- at least one secondary fluid channel, the at least one secondary fluid channel for transporting a gas or liquid fluid, the at least one secondary fluid channel being disposed on the first face of the substrate and having a plurality of perforations oriented away from the substrate for emitting a fluid directly to the outside environment;
- wherein the water channel, CO2 gas channel, light channel, and at least one secondary fluid channel are oriented parallel to each other;
- wherein the perforations of the water channel, the CO2 gas, channel have a predetermined aperture size, the size of the CO2 gas perforations being lesser than the size of the water channel perforations;
- wherein the substrate has three longitudinally oriented sets of perforations, a first set of perforations being disposed between the water channel and the CO2 gas channel, a second set of perforations being disposed between the CO2 gas channel and the light channel, and a third set of perforations being disposed between the light channel and the at least one secondary fluid channel, whereby the channels may be selectively separated from each other.

* * * * *